US010255785B1

(12) United States Patent
Huang et al.

(10) Patent No.: US 10,255,785 B1
(45) Date of Patent: Apr. 9, 2019

(54) INTELLIGENT ENVIRONMENTAL AND SECURITY MONITORING SYSTEM

(71) Applicant: Taiwan Semiconductor Manufacturing Co., Ltd., Hsinchu (TW)

(72) Inventors: Chun-Jung Huang, Tuku Township (TW); Kuang-Huan Hsu, Hsinchu (TW); Yung-Lin Hsu, Hsinchu (TW)

(73) Assignee: Taiwan Semiconductor Manufacturing Co., Ltd., Hsin-Chu (TW)

( * ) Notice: Subject to any disclaimer, the term of this patent is extended or adjusted under 35 U.S.C. 154(b) by 0 days.

(21) Appl. No.: 15/835,327

(22) Filed: Dec. 7, 2017

(51) Int. Cl.
| | |
|---|---|
| *H01L 21/66* | (2006.01) |
| *G08B 21/18* | (2006.01) |
| *H01L 21/677* | (2006.01) |
| *G01N 27/414* | (2006.01) |
| *H04W 4/38* | (2018.01) |
| *G05D 1/02* | (2006.01) |

(52) U.S. Cl.
CPC ......... *G08B 21/18* (2013.01); *G01N 27/4141* (2013.01); *G05D 1/0238* (2013.01); *H01L 21/67724* (2013.01); *H04W 4/38* (2018.02); *B65G 2201/0297* (2013.01)

(58) Field of Classification Search
CPC .......... G05B 19/4189; H01L 21/67733; H01L 21/67253; H01L 21/67294; Y02P 90/28
See application file for complete search history.

(56) References Cited

U.S. PATENT DOCUMENTS

| | | | | |
|---|---|---|---|---|
| 2004/0228712 A1* | 11/2004 | Nam | ................... | B25J 15/0052 |
| | | | | 414/416.03 |
| 2007/0276540 A1* | 11/2007 | Okuda | ................. | G05D 1/0272 |
| | | | | 700/245 |
| 2011/0271839 A1* | 11/2011 | Kim | ....................... | B01D 53/72 |
| | | | | 96/111 |
| 2012/0027544 A1* | 2/2012 | Wang | ................ | H01L 21/67253 |
| | | | | 414/222.01 |
| 2016/0188977 A1* | 6/2016 | Kearns | ............... | G06K 9/00664 |
| | | | | 348/113 |

* cited by examiner

*Primary Examiner* — Hongmin Fan
(74) *Attorney, Agent, or Firm* — Duane Morris LLP

(57) ABSTRACT

Disclosed is a method and a system for monitoring of environment and security in a fabrication facility. In one embodiment, a method comprising: transporting an automated material handling system (AMHS) vehicle from a first position to a second position; and detecting at least one parameter using at least one sensor located on the AMHS vehicle to determine at least one environmental or security condition between the first and second positions.

20 Claims, 4 Drawing Sheets

INTELLIGENT ENVIRONMENTAL AND SECURITY MONITORING SYSTEM

CROSS-REFERENCE TO RELATED APPLICATIONS

The present application claims priority benefit of U.S. Provisional Application No. 62/585,459, filed on Nov. 13, 2017, the contents of which are incorporated by reference in its entirety.

BACKGROUND

The quality, consistency, and cost of machined products depend on a complex combination of the performance of process steps and equipment. Manufacturing of complex, high-value products typically require lengthy trial-and-error procedures and result in wasted resources due to inconsistencies and/or uncertainties in material properties and/or behavior of manufacturing equipment under various manufacturing conditions. These inconsistencies or uncertainties, at least in part, result from the adverse effects caused by environmental conditions, e.g., contaminants, that may be introduced or generated during the manufacturing process. Furthermore, contaminants such as micro/nano-scale aerosol particles (<100 nanometers to a few micrometers) can also increase health risks to operators in a fabrication facility.

Within a typical semiconductor fabrication facility (FAB) environment, contaminants can be generated in the form of gases, chemical vapors, micro/nano-scale aerosol particles, airborne molecular contamination, etc. Micro/nano-scale aerosol particles containing a variety of ionic species in a cleanroom may arise from a number of sources including human behavior (e.g., hygiene, clothing, etc.), cleanroom airflow, equipment, materials, and nanomaterials synthesis processes. They can be either released directly or formed during atmospheric chemical reactions, such as for instance from evaporating heated chemicals/solvents, and gas leakage/outgassing from thin film and its processing equipment, etc. In addition to micro/nano-scale aerosol particles, airborne molecular contamination (AMC) is also a concern during semiconductor manufacturing processes. Such organic contamination may cause adverse effects on production tools and consequently increase costs for FAB operators. The AMC level in cleanroom environments is predominately created by internal sources of solvents and acetic acid, re-entrainment of exhaust air, aromatic compounds, as well as material outgassing. In addition, spills, leaks and mishandling can occur and can cause serious costs in terms of wafer loss and tool-down time.

A contamination-free manufacturing environment is desirable and can be achieved by source control/monitoring in combination with filtration solutions in air handling systems. Continuous, online, and real-time monitoring of these contaminant levels helps identifying sources, stabilizes production and prevents unexpected shortfalls of the service life of filtration units. Traditional environmental monitoring in a FAB environment, however, is expensive and time consuming, relying on a deployment of human-power for sample collection and dedicated equipment for measurement/characterization. Additionally, traditional environmental monitoring techniques do not provide continuous real-time monitoring, which means that when measurement results are provided for review, the condition of the FAB facility may have already changed.

In addition to monitoring contaminants (e.g., types and levels) in the cleanroom, close supervision and observation of operators and other persons, including visitors and third-party contractors, who enter in and out of a FAB facility, is also necessary. Traditional observational surveillance methods are typically implemented using stationary cameras located at predetermined locations within the facility. Installing a large number of cameras to achieve adequate coverage, however, can be very costly. Furthermore, although this traditional method can detect unauthorized persons or activities, it does not provide opportunities to detect unauthorized communications, such as video/picture recording, voice communication, and file uploads/downloads.

Therefore, there exists a need for an easier, faster and cheaper technology to realize a real-time monitoring of environment contaminant levels and security in a semiconductor fabrication facility.

BRIEF DESCRIPTION OF THE DRAWINGS

Aspects of the present disclosure can be understood from the following detailed description when read with the accompanying figures. It should be noted that various features are not necessarily drawn to scale. In fact, the dimensions and geometries of the various features may be arbitrarily increased or reduced for clarity of illustration.

DETAILED DESCRIPTION OF EXEMPLARY EMBODIMENTS

Figure 1:
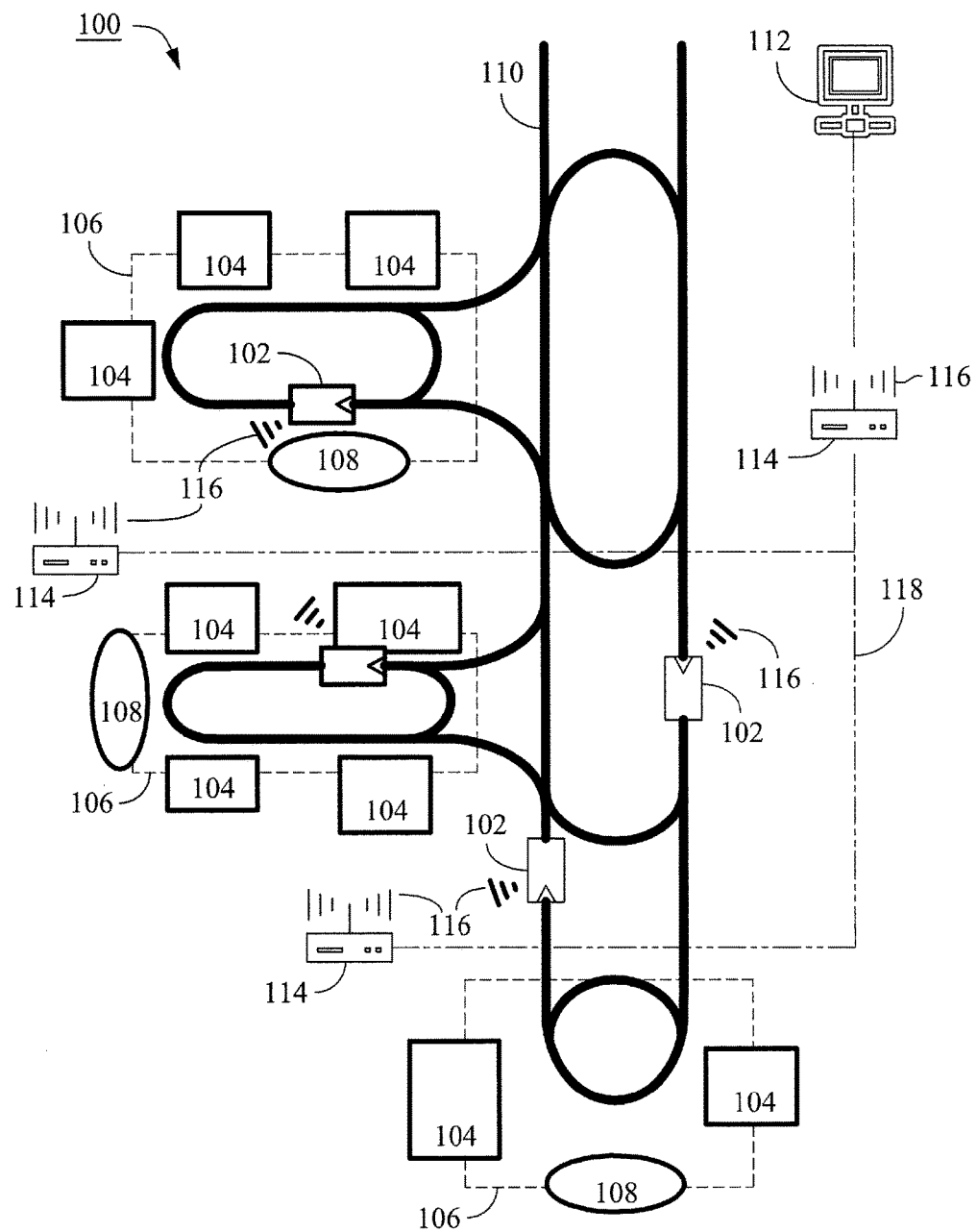
FIG. 1 illustrates a schematic of a semiconductor fabrication facility equipped with a plurality of automated material handling system (AMHS) vehicles configured to transport wafers between equipment for processing and/or measurement while carrying a variety of sensors and detectors for monitoring environment and security parameters, in accordance with some embodiments of the present disclosure.

The following disclosure describes various exemplary embodiments for implementing different features of the subject matter. Specific examples of components and arrangements are described below to simplify the present disclosure. These are, of course, merely examples and are not intended to be limiting. For example, it will be understood that when an element is referred to as being "connected to" or "coupled to" another element, it may be directly connected to or coupled to the other element, or one or more intervening elements may be present.

This description of the exemplary embodiments is set to be understood in connection with the figures of the accompanying drawing, which are to be considered part of the entire written description. In the description, relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation.

The presented disclosure provides various embodiments of a method and a system for monitoring environment parameters (e.g., micro/nano-scale aerosol particles and AMC containment types/levels, temperature, humidity, and magnetic field) and security (e.g., unauthorized persons and activities including unauthorized wireless communication) in a semiconductor fabrication facility. During the fabrication of semiconductor devices, semiconductor wafers are subjected to multiple processing steps performed by different processing equipment. Fabrication facilities generally include an automated material handling system (AMHS) for transporting the wafers between different processing equipment, or between processing equipment and measurement equipment. In some embodiments, a real-time continuous monitoring system is integrated on one or more AMHS vehicles, allowing monitoring of environmental contaminant levels together with one or more other physical parameters. Thus, environmental and/or security parameters can be measured throughout a fabrication facility without introducing expensive and bulky equipment to perform these measurements. Moving AMHS vehicles equipped with environmental/security monitoring systems provide complementary patrols in the fabrication facility in addition to the existing stationary security monitoring systems at predetermined locations (e.g., identification card, CCTV camera, etc.) by detecting unauthorized persons or activities (e.g., unauthorized communication, access, and data/file transfer outside of the facility such as on mobile devices or other type of electronic communication devices). Accordingly, the above-mentioned environmental and security issues maybe advantageously avoided.

FIG. 1 illustrates a schematic of a semiconductor fabrication facility 100 equipped with a plurality of AMHS vehicles 102 transporting wafers between equipment 104 for processing and/or measurement while carrying a plurality of sensors and detectors for monitoring environmental and security conditions, in accordance with some embodiments of the present disclosure. In a semiconductor fabrication facility 100, equipment 104 with similar functions is generally clustered in process bays 106. At least one storage station 108 is typically included and located at one end of a process bay 106. An automated inter-bay transport of wafer containers by AMHS vehicles 102 between storage stations 108 of process bays 106 can be guided on overhead transport rails 110. Each of storage stations 108 contains a number of vertically-stacked storage bins for storing semiconductor wafers or wafer containers, in certain embodiments. An AMHS vehicle transports wafers and wafer containers can be in the form of an overhead hoist transport (OHT), overhead shuttle (OHS), automated guided vehicle (AGV), rail guided vehicle (RGV), conveyor system, or a combination thereof, in accordance with various embodiments.

Wafers are processed or measured at the respective equipment 104. Traditionally, when a process or a measurement is completed on a wafer, an operator can manually unload the wafer from equipment 104 and store the wafer in a wafer container (not shown) such as a Front Opening Unified Pod (FOUP) and a Front Opening Shipping Box (FOSB), and then transfer the FOUP or FOSB to a storage station 108 of a process bay 106. In some embodiment, a robotic mechanical transfer mechanism can be also implemented to replace the manual operation. In some embodiments, dedicated inter-bay and intra-bay AMHS vehicles 102 can be used to transfer wafer containers on a transport rail 110. In particular, the inter-bay AMHS vehicles 102 move containers between storage stations 108 in different process bays 106, whereas intra-bay AMHS vehicles 102 move containers between storage stations 108 and equipment 104, or between equipment 104 within the same process bay 106, in accordance with various embodiments.

In some embodiments, an intra-bay AMHS vehicle 102 picks up a FOUP from a first storage station 108 and transports it on rail 110 to a second storage stations 108 in the first process bay 106 or a second different process bay 106, in accordance with some embodiments, where the next processing or measurement step is to be performed. The wafers in the FOUP stay in the second storage station 108 while waiting for the next processing or measurement step. Then, an operator from the second storage station 108 can manually load the wafer in to the corresponding equipment 104. In some embodiments, an AMHS vehicle 102 can automatically pick up the FOUP, transport the FOUP on rail 110, and load the wafer into the corresponding equipment 104 for the next processing or measurement. Once all required processes on the wafers in the FOUP is complete, the wafers are stored back in the FOUP and transported by the same or a different AMHS vehicle 102 on the transport rail 110 to a destination such as a test facility or a packaging facility. Each time a FOUP is transferred from one place to another, a barcode (e.g., RFID) on the FOUP can be scanned by a barcode reader (not shown) along the transport rail 110 or in the storage station 108. The transfer of the wafers contained therein is recorded in a computer system for operating the AMHS vehicles 102. When a piece of equipment completes a step of a process on a wafer, a host computer 112 determines whether the wafer should be sent to one of the storage stations 108. For example, if a nearby first storage station 108 is full, the wafer is sent to a nearby storage station 108 in the same or a different process bay 106. For another example, if the next step of the process will be performed on the wafer immediately, the wafer may be sent directly to its destination equipment, in accordance with various embodiments.

When traveling on the transport rail 110 between equipment 104 within the same process bay 106 or between process bays 106, a plurality of sensors on AMHS vehicles 102 can provide real-time monitoring of environmental parameters, such as for instance temperature, humidity, magnetic field, contaminant levels (e.g., micro/nano-scale particles and AMC), etc. in a FAB environment. In some embodiments, the plurality of detectors for security monitoring (e.g., surveillance cameras and radio frequency signal detectors) can be also integrated onto the AMHS vehicles 102 providing complementary security patrols in the FAB facility in addition to the existing stationary security monitoring systems at predetermined locations. Descriptions of each type of sensors and detectors are discussed in further detail below with reference to FIG. 2. The AMHS vehicles 102 can directly communication with a nearby wireless router 114 through a wireless communication signal 116. Signals containing measurement data from the plurality of sensors and detectors can be transmitted from the wireless routers 114 to a host computer 112 for data logging and analysis through high-speed wired communication network 118.

Figure 2A:
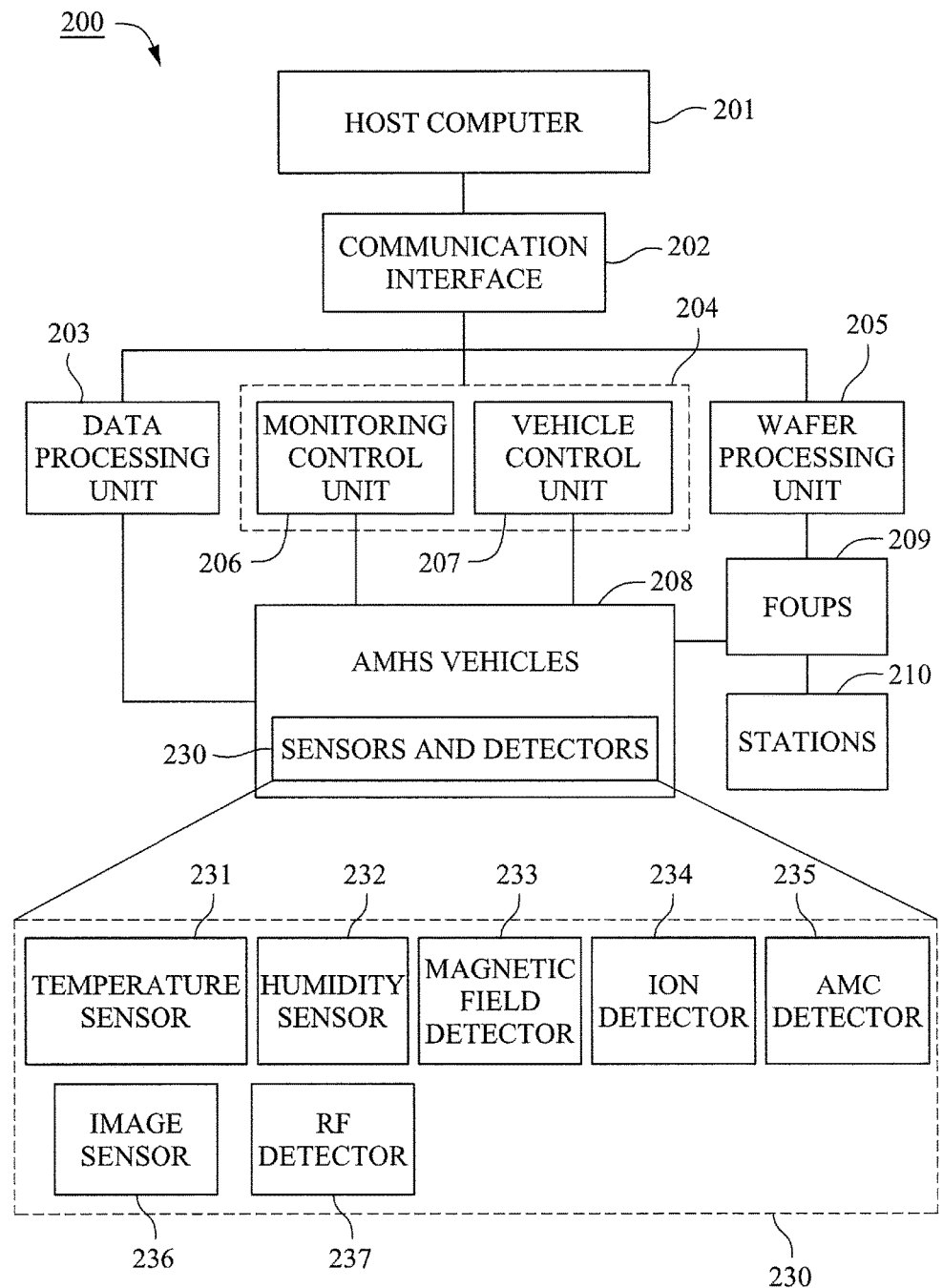
FIG. 2A illustrates a block diagram showing an exemplary configuration of the monitoring system integrated into an AMHS system in a semiconductor fabrication facility, in accordance with some embodiments of the present disclosure.

FIG. 2A illustrates a block diagram showing an exemplary configuration of a monitoring system 200 integrated into an AMHS system in a semiconductor fabrication facility, in accordance with some embodiments of the present disclosure. The monitoring system 200 includes a host computer 201, a communication interface 202, a data processing unit 203, a transport vehicle unit 204, and a wafer processing unit 205. The host computer 201 is used for real-time measurement control and data display of measurement results from the plurality of sensors and detectors on the AMHS vehicles transporting wafer containers on a transport rail in a FAB facility, as discussed above. In some embodiments, the host computer 201 can be also used for centralized real-time monitoring of IOT (internet-of-things) devices and systems. The transport vehicle unit 204 comprises a monitoring control unit 206 and a vehicle control unit 207. The vehicle control unit 207 in the wafer processing control unit 205 controls and operates AMHS vehicles 208 to transport FOUPs 209, e.g., between stations 210. In some embodiments, the AMHS vehicles 208 are configured to provide loading, unloading and shelving functions to wafers to and from stations 210 in different process bays. In some embodiments, each of the AMHS vehicles 208 comprises a robotic arm and/or hoist to provide movement in horizontal and vertical directions to be able to mechanically couple to the FOUPs 209. Station 210 comprises equipment for semiconductor processing or measurement including but not limited to cleaning, rinsing, polishing, photolithography, developing, deposition, etching, electrical measurement equipment, optical measurement equipment etc., in accordance with various embodiments. In some embodiments, the station 210 can be a storage station.

The AMHS vehicle 208 carries a plurality of sensors and detectors 230, in accordance with various embodiments. The plurality of sensors and detectors 230 comprises one or more of the following: a temperature sensor 231, a humidity sensor 232, a magnetic field detector 233, a particle detector 233, and AMC detector 232 for environmental monitoring. In some embodiments, the plurality of sensors and detectors 230 can provide real-time continuous monitoring of environment parameters, including temperature, humidity, magnetic field strength/direction, inorganic ion type/concentration in micro/nano-scale aerosol particles, organic contaminant concentration, particle concentration etc. In some embodiments, the plurality of sensors and detectors 230 on the AMHS vehicle 208 also comprises an image sensor (e.g., camera) 236 and a radio frequency (RF) signal detector 237 for security monitoring, which can detect unauthorized operations of equipment, unauthorized persons or activities in a FAB facility including unauthorized wireless communications.

In some embodiments, different types of temperature sensors 231 can be implemented, including contact and non-contact temperature sensors depending on performance requirements, e.g., detection range, sensitivity, accuracy, response time, repeatability, size, power consumption, cost, etc. In some embodiments, a contact type temperature sensor can be a thermostat including two different metals (e.g., nickel, copper, tungsten, aluminum, etc.), a thermistor typically including ceramic materials (e.g., oxides of nickel, manganese, cobalt, etc.), a thin film resistive sensor typically including thin high-purity conducting metals (e.g., platinum, copper, nickel, etc.), a thermocouple including two different metals (e.g., copper, iron, a variety of metal alloys, etc.) and two junctions, semiconductor junctions sensors, a fiber-optic sensor including a semiconductor crystal (e.g., GaAs) which shifts its transmission spectrum with temperature, and the like. In some embodiments, a non-contact type temperature sensor can be a pyrometer typically including a photodetector responding to a certain band of spectrum (e.g., an infra-red radiation sensor).

In some embodiments, a humidity sensor 232 can be selected from one of the following: a capacitive sensor including a polymer or metal oxide sandwiched between two conductive electrodes, a resistive sensor including a hygoscopic media and noble metal electrodes (e.g., polymer, salt, treated substrate, etc.), and a thermal conductivity sensor including two thermistors and at least a resistive heater. The selection of a proper humidity sensor can be determined by the accuracy, repeatability, long-term stability, resistance to chemical contaminants, size, cost, lifetime, etc., in accordance with various embodiments.

Depending on the magnetic field strength, different magnetic field detectors 233 can be selected, such as low-field (<1 microgauss), medium-field (1 microgauss~10 gauss), and high-field (>10 gauss). A magnetic field detector 233 can be but not limited to, a superconducting quantum interference device (SQUID) sensor, a fiber-optic sensor, a optically pumped sensor, a nuclear procession sensor, a search-coil sensor, an anisotropic magnetoresistive sensor, a flux gate sensor, a magnetodiode sensor, a magnetotransistor sensor, a magneto-optical sensor, a giant magnetoresistive (GMR) sensor, a Reed switch, a Lorentz force device, a hall-effect sensor, a microelectrochemical (MEMS) sensor, and the like.

In some embodiments, an ion detector 234 can be used for detecting contaminants in air within a FAB facility, including ionic species in forms of micro/nano-scale aerosol particles such as for instance $F^-$, $Cl^-$, $NO_3^-$, $PO_4^{3-}$, $SO_4^{2-}$, $NH_4^+$, and $NO_2^-$. In some other embodiments, an AMC detector 235 can detect organic species such as for instance acetone/IPA, Propylene Glycol Methyl Ether (PGME), toluene, propylene glycol monomethyl ether acetate (PGMEA). In some embodiments, contaminant levels of these ionic and organic species in a typical FAB facility can be in a range of a few parts per million (ppm) and a few tens of ppm. In some embodiments, the ideal detectors 234 and 235 for detecting contaminant levels should have the following properties, including low drift and noise level, high sensitivity, fast response time, wide linear dynamic range, low dead volume, insensitivity to measurement conditions (e.g., solvent, flow rate, and temperature), simple operation, high reliability, compact size/weight, and low power consumption, in accordance with various embodiments.

In some embodiments, at least one of the following ion detectors 234 can be used, such as for instance electrical conductivity detector, amperometric detector, and mass spectrometer. In some embodiments, the ion detector 234 can be an electrochemical sensor wherein a gaseous sample (e.g., air sample from a FAB environment) can be bubbled in an aqueous solution. Ions, especially cations that are reduced on an electrode in the electrochemical sensor by applying a reductive voltage can be oxidized and return to the solution at a characteristic voltage and concentration can be measured by measuring the current density, in accordance with some embodiments.

In some embodiments, the ion detector 234 can be a chromatography instrument. A chromatography typically together with a mass spectrometry can be used to provide detailed analysis of contamination species and their concentration. Qualitative and quantitative analysis of common ions in their different forms and matrices in trace and ultra-trace concentrations can be detected using this method. In some embodiments, chromatography that can be used includes liquid and/or gas chromatography. Typically, chromatography instrumentation includes: pump, injector, column, suppressor, detector and recorder or data system. All materials used in the system have to be inert to many organic solvents or aqueous solution with extreme pH values. In some embodiments, reservoirs and distribution systems (e.g., tubing, valves, pump, columns, sampling devices, and detectors) that may come in contact with the solution can be made of plastic, e.g., polyether ether-ketone (PEEK), or glass. In some embodiments, a vacuum can be implemented within a reservoir and helium gas purging can be used to eliminate signal noise from microscopic gas bubbles in the solution. In some embodiments, various type of pumps can be selected to flow liquid to the detector, e.g., constant flow pump, reciprocating piston pump, dual piston pump, etc., depending on the type of flow and flow rate. In some embodiments, cations can be separated on the cation-exchange column and anions can be separated on the anion-exchange column. In some embodiments, eluent composition can be adjusted to adjust the detection limit and separation time.

In certain embodiments, the chromatography instrument can be a Thermal desorption (TD) coupled with a gas chromatography with a mass spectrometry (GC-MS). The TD-GCMS can be used to as a AMC detector to detect volatile AMC contaminants. With TD-GCMS, sorption tubes are heated to volatilize collected organics which are then analyzed by GC-MS. In some embodiments, an AMC detector 235 can be a thermal conductivity sensor based on the detection of different heat conductivity of gases and their concentration in air. In some embodiments, air samples can be concentrated by using impingers or sorption tubes in order to monitor trace contaminants in air, wherein an impinger is a water-filled tube through which the air sample is bubbled. Airborne contaminants accumulate in the water, which can be then analyzed, according to certain embodiments.

In another embodiment, a Cavity Ring Down Spectroscopy (CDRS) and Ion Mobility Spectrometry (IMS) that have short response time can be used for continuous contaminant monitoring in an ion detector 234 and/or an AMC detector 235. CDRS has been developed as a sensitive, rapid detector for gases (e.g., ammonia) with an accuracy and sensitivity less than 1 parts per billion (ppb) within seconds to minutes. Typically, the CDRS measures light absorption in a mirrored cavity that effectively lengthens the light path. IMS can be used for detecting both ionic and organic species with a short response time but with limited ability to identify compounds depending on the application, in accordance with various embodiments.

In some embodiments, the ion detector 234 and the AMC detector 235 can be a flame ionization detector (FID), a combustible gas indicator (CGI), portable infrared (IR) spectrophotometer, ultraviolet (UV) photoionization detector (PID), gas chromatography and nitrogen/phosphorus detector (GC/NPD), inductively coupled plasma atomic emission spectrometry (ICP-AES), GC with a thermal energy analyzer (GC-TEA), GC-using an electrical conductivity detector (GC-ECD). In some embodiments, a plurality of ion and AMC detectors and a combination thereof can be used according to the type of contaminants and their concentrations.

Sampling media in the form of filter or sorbent (not shown) largely depends on the type of contaminants. For example, charcoal can be used for absorbing organic species (e.g., AMC), anions species (negatively charged ions) can be absorbed on prewashed silica gel/beads and mixed cellulose ester filter (MCEF). Passive air collection or a pump which can actively draw air through a filter or sorbent can be used, according to certain embodiments, depending on the contaminant concentration and measurement requirements. In some embodiments, an active sample collection using a pump at a flow rate that is large enough to concentrate the contaminant on the sorbent and to minimize the detection time is advantageous over a passive sample collection.

In some embodiments, a facility surveillance is conducted by an image sensor (i.e., camera) 236 which can be also integrated to the AMHS vehicle to detect unauthorized persons and/or activities. An image sensor 236 based on visible light can be a semiconductor charge-coupled devices (CCD), active pixel sensor in complementary metal-oxide-semiconductor (CMOS), or sensors that are based on detecting optical signals with wavelengths other than that of the visible light, in accordance with various embodiments. Functions, such as for example camera controls (e.g., tilt, record, zoom, pan, etc.), and motion/face detection can be provided by a control software based on a predefined algorithm. Algorithms for processing video data obtained from the image sensor are implemented in onboard computers and/or processors or video data can be transmitted through a communication interface 202 (e.g., wired or wireless or a combination) to a host computer 201 for processing, in accordance with various embodiments.

In some embodiments, a radio frequency (RF) detector 237 can be also integrated to the AMHS vehicle to detect any unauthorized wireless communications using signals including but not limited to cellular signals, GPS signals, Wi-Fi signals, Bluetooth signals, radio signals, and/or any other type of modulated wireless signals in a FAB facility. An RF detector can be one of the following sensors including but not limited to, a diode sensor including a CMOS (complementary metal oxide semiconductor) Schottky diode, a MOSFET (metal oxide semiconductor field effect transistor) diode, etc. In some embodiment, the RF detector 237 can be a thermal RF sensor including at least one temperature sensor, a receiver type detector including a series of processing circuits e.g., attenuator, mixture, amplifier, filter, A/D convertor, etc. Selection of the RF detector 237 is based on the detection frequency, power consumption, etc.

In addition to the plurality of sensors and detectors on the AMHS vehicles, monolithic signal conditioning circuits is typically needed in the data processing unit 203 including filters, operational amplifiers, signal conditioners, etc., for realizing functions including scaling, amplification, linearization, and A/D conversion.

Figure 2B:
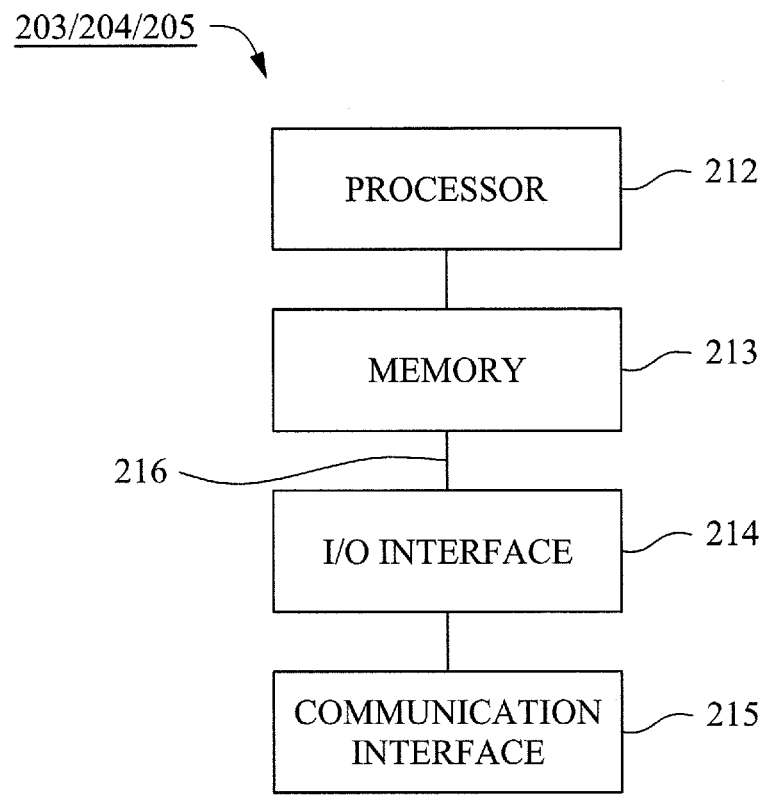
FIG. 2B illustrates a block diagram of a controller utilized in the monitoring system shown in FIG. 2A, in accordance with some embodiments of the present disclosure.

FIG. 2B illustrates a block diagram of the controller units 203/204/205 of the system 200 shown in FIG. 2A, in accordance with some embodiments of the present disclosure. The data processing unit 203, the vehicle control unit 204, and wafer processing unit 205 in the system 200 may each comprise a processor, a memory, an input/output interface (hereinafter "I/O interface"), a communications interface, and a system bus. In some embodiments, components in these units in the system 200 may be combined or omitted such as, for example, not including the communications interface. In some embodiments, the control units 203, 204 and 205 of the system 200 may comprise other components not shown in FIG. 2B. For example, these units 203, 204, and 205 of the system 200 also may comprise a power subsystem providing power to the light source. In other embodiments, these units 203, 204 and 205 of the system 200 may comprise several instances of the components shown in FIG. 2B.

The processor 212 may comprise any processing circuitry operative to control the operations and performance of the units 203, 204 and 205 of the system 200. In various aspects, the processor 212 may be implemented as a general purpose processor, a chip multiprocessor (CMP), a dedicated processor, an embedded processor, a digital signal processor (DSP), a network processor, an input/output (I/O) processor, a media access control (MAC) processor, a radio baseband processor, a co-processor, a microprocessor such as a complex instruction set computer (CISC) microprocessor, a reduced instruction set computing (RISC) microprocessor, and/or a very long instruction word (VLIW) microprocessor, or other processing device. The processor subsystem 406 also may be implemented by a controller, a microcontroller, an application specific integrated circuit (ASIC), a field programmable gate array (FPGA), a programmable logic device (PLD), and so forth.

In various aspects, the processor 212 may be arranged to run an operating system (OS) and various applications. Examples of an OS comprise, for example, operating systems generally known under the trade name of Apple OS, Microsoft Windows OS, Android OS, and any other proprietary or open source OS. Examples of applications comprise, for example, a telephone application, a camera (e.g., digital camera, video camera) application, a browser application, a multimedia player application, a gaming application, a messaging application (e.g., email, short message, multimedia), a viewer application, and so forth.

In some embodiments, at least one non-transitory computer-readable storage medium is provided having computer-executable instructions embodied thereon, wherein, when executed by at least one processor, the computer-executable instructions cause the at least one processor to perform embodiments of the methods described herein. This computer-readable storage medium can be embodied in the memory 213.

In some embodiments, the memory 213 may comprise any machine-readable or computer-readable media capable of storing data, including both volatile/non-volatile memory and removable/non-removable memory. The memory 213 may comprise at least one non-volatile memory unit. The non-volatile memory unit is capable of storing one or more software programs.

The software programs may contain, for example, applications, user data, device data, and/or configuration data, or combinations therefore, to name only a few. The software programs may contain instructions executable by the various components of the units 203, 204 and 205 of the system 200.

For example, memory 213 may comprise read-only memory (ROM), random-access memory (RAM), dynamic RAM (DRAM), Double-Data-Rate DRAM (DDR-RAM), synchronous DRAM (SDRAM), static RAM (SRAM), programmable ROM (PROM), erasable programmable ROM (EPROM), electrically erasable programmable ROM (EEPROM), flash memory (e.g., NOR or NAND flash memory), content addressable memory (CAM), polymer memory (e.g., ferroelectric polymer memory), phase-change memory (e.g., ovonic memory), ferroelectric memory, silicon-oxide-nitride-oxide-silicon (SONOS) memory, disk memory (e.g., floppy disk, hard drive, optical disk, magnetic disk), or card (e.g., magnetic card, optical card), or any other type of media suitable for storing information.

In one embodiment, the memory 213 may contain an instruction set, in the form of a file for executing a method of generating one or more timing libraries as described herein. The instruction set may be stored in any acceptable form of machine readable instructions, including source code or various appropriate programming languages. Some examples of programming languages that may be used to store the instruction set comprise, but are not limited to: Java, C, C++, C#, Python, Objective-C, Visual Basic, or .NET programming. In some embodiments a compiler or interpreter is comprised to convert the instruction set into machine executable code for execution by the processor 212.

In some embodiments, the I/O interface 214 may comprise any suitable mechanism or component to at least enable a user to provide input to the units 203, 204 and 205 and the units 203, 204 and 205 to provide output to the user. For example, the I/O interface 214 may comprise any suitable input mechanism, including but not limited to, a button, keypad, keyboard, click wheel, touch screen, or motion sensor. In some embodiments, the I/O interface 214 may comprise a capacitive sensing mechanism, or a multi-touch capacitive sensing mechanism (e.g., a touch screen).

In some embodiments, the I/O interface 214 may comprise a visual peripheral output device for providing a display visible to the user. For example, the visual peripheral output device may comprise a screen such as, for example, a Liquid Crystal Display (LCD) screen, incorporated into the units 203, 204 and 205 of the system 200. As another example, the visual peripheral output device may comprise a movable display or projecting system for providing a display of content on a surface remote from the units 203, 204 and 205 of the system 200. In some embodiments, the visual peripheral output device can comprise a coder/decoder, also known as a Codec, to convert digital media data into analog signals. For example, the visual peripheral output device may comprise video Codecs, audio Codecs, or any other suitable type of Codec.

The visual peripheral output device also may comprise display drivers, circuitry for driving display drivers, or both. The visual peripheral output device may be operative to display content under the direction of the processor 212. For example, the visual peripheral output device may be able to play media playback information, application screens for application implemented on the units 203, 204 and 205 of the topological scan system 200, information regarding ongoing communications operations, information regarding incoming communications requests, or device operation screens, to name only a few.

In some embodiments, the communications interface 215 may comprise any suitable hardware, software, or combination of hardware and software that is capable of coupling the units 203, 204 and 205 of the system 200 to one or more networks and/or additional devices (such as, for example, the environment and security detectors 230, AMHS transport vehicles 208, FOUPs 209 and equipment 210). The communications interface 215 may be arranged to operate with any suitable technique for controlling information signals using a desired set of communications protocols, services or operating procedures. The communications interface 215 may comprise the appropriate physical connectors to connect with a corresponding communications medium, whether wired or wireless.

Systems and methods of communication comprise a network, in accordance with some embodiments. In various aspects, the network may comprise local area networks (LAN) as well as wide area networks (WAN) including without limitation Internet, wired channels, wireless channels, communication devices including telephones, computers, wire, radio, optical or other electromagnetic channels, and combinations thereof, including other devices and/or components capable of/associated with communicating data. For example, the communication environments comprise in-body communications, various devices, and various modes of communications such as wireless communications, wired communications, and combinations of the same.

Wireless communication modes comprise any mode of communication between points (e.g., nodes) that utilize, at least in part, wireless technology including various protocols and combinations of protocols associated with wireless transmission, data, and devices. The points comprise, for example, wireless devices such as wireless headsets, audio and multimedia devices and equipment, such as audio players and multimedia players, telephones, including mobile telephones and cordless telephones, and computers and computer-related devices and components, such as printers, network-connected machinery such as a circuit generating system, and/or any other suitable device or third-party device.

Wired communication modes comprise any mode of communication between points that utilize wired technology including various protocols and combinations of protocols associated with wired transmission, data, and devices. The points comprise, for example, devices such as audio and multimedia devices and equipment, such as audio players and multimedia players, telephones, including mobile telephones and cordless telephones, and computers and computer-related devices and components, such as printers, network-connected machinery, and/or any other suitable device or third-party device. In various implementations, the wired communication modules may communicate in accordance with a number of wired protocols. Examples of wired protocols may comprise Universal Serial Bus (USB) communication, RS-232, RS-422, RS-423, RS-485 serial protocols, FireWire, Ethernet, Fiber Channel, MIDI, ATA, Serial ATA, PCI Express, T-1 (and variants), Industry Standard Architecture (ISA) parallel communication, Small Computer System Interface (SCSI) communication, or Peripheral Component Interconnect (PCI) communication, to name only a few examples.

Accordingly, in various aspects, the communications interface 215 may comprise one or more interfaces such as, for example, a wireless communications interface, a wired communications interface, a network interface, a transmit interface, a receive interface, a media interface, a system interface, a component interface, a switching interface, a chip interface, a controller, and so forth. When implemented by a wireless device or within wireless system, for example, the communications interface 215 may comprise a wireless interface comprising one or more antennas, transmitters, receivers, transceivers, amplifiers, filters, control logic, and so forth.

In various aspects, the communications interface 215 may provide voice and/or data communications functionality in accordance a number of wireless protocols. Examples of wireless protocols may comprise various wireless local area network (WLAN) protocols, including the Institute of Electrical and Electronics Engineers (IEEE) 802.xx series of protocols, such as IEEE 802.11a/big/n, IEEE 802.16, IEEE 802.20, and so forth. Other examples of wireless protocols may comprise various wireless wide area network (WWAN) protocols, such as GSM cellular radiotelephone system protocols with GPRS, CDMA cellular radiotelephone communication systems with 1×RTT, EDGE systems, EV-DO systems, EV-DV systems, HSDPA systems, and so forth. Further examples of wireless protocols may comprise wireless personal area network (PAN) protocols, such as an Infrared protocol, a protocol from the Bluetooth Special Interest Group (SIG) series of protocols, including Bluetooth Specification versions v1.0, v1.1, v1.2, v2.0, v2.0 with Enhanced Data Rate (EDR), as well as one or more Bluetooth Profiles, and so forth. Yet another example of wireless protocols may comprise near-field communication techniques and protocols, such as electro-magnetic induction (EMI) techniques. An example of EMI techniques may comprise passive or active radio-frequency identification (RFID) protocols and devices. Other suitable protocols may comprise Ultra Wide Band (UWB), Digital Office (DO), Digital Home, Trusted Platform Module (TPM), ZigBee, and so forth.

In some embodiments, the units 203, 204 and 205 of the system 200 may comprise a system bus 216 that couples various system components including the processor 212, the memory 213, and the I/O interface 214. The system bus 216 can be any of several types of bus structure(s) including a memory bus or memory controller, a peripheral bus or external bus, and/or a local bus using any variety of available bus architectures including, but not limited to, 9-bit bus, Industrial Standard Architecture (ISA), Micro-Channel Architecture (MSA), Extended ISA (EISA), Intelligent Drive Electronics (IDE), VESA Local Bus (VLB), Peripheral Component Interconnect Card International Association Bus (PCMCIA), Small Computers Interface (SCSI) or other proprietary bus, or any custom bus suitable for computing device applications.

Figure 3:
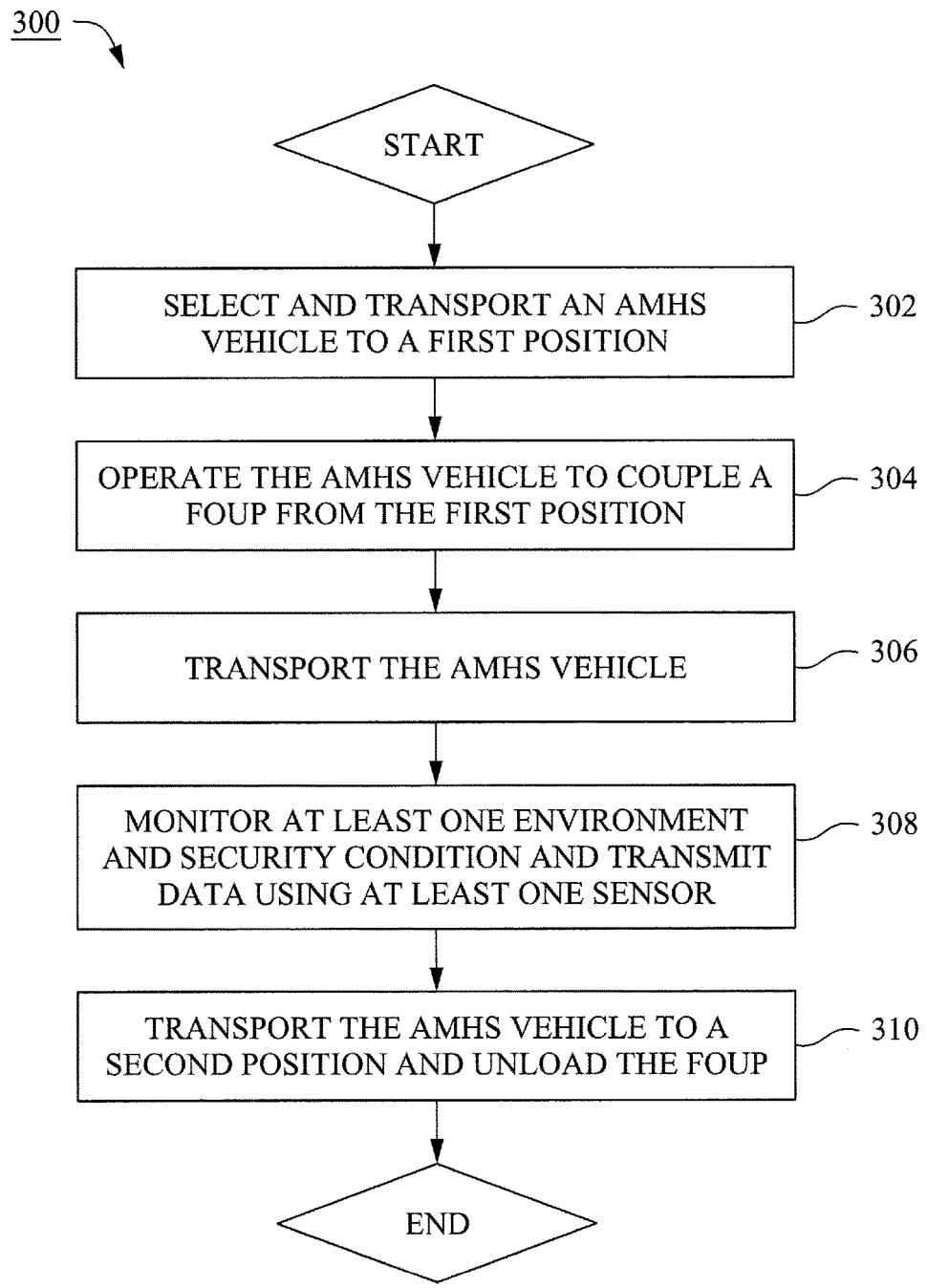
FIG. 3 illustrates a flow chart of a method for conducting environment and security monitoring in a semiconductor fabrication facility, in accordance with various embodiments of the present disclosure.

FIG. 3 illustrates a flow chart of a method 300 for conducting environment and security monitoring using the presented system on an AMHS vehicle in a semiconductor fabrication facility, in accordance with various embodiments of the present disclosure. The process 300 starts with operation 302, wherein an AMHS vehicle is selected, controlled and transported by a host computer to a first loading position, such as for instance a loading port of a storage station, a processing equipment or a measurement equipment at a process bay. Then the process 300 continues with operation 304, wherein the AMHS vehicle is operated to mechanically couple with a FOUP at the first loading position based on the location information of the FOUP in a storage station. In some embodiments, a driver program can be used to determine the position of the FOUP on the shelf and to pick of the FOUP from the corresponding position. In some embodiments, the driver can also determine the destination of the FOUP. In certain embodiments, the host computer can send a command to the AMHS vehicle to pick up the FOUP from the first position (e.g., a first processing station, a first measurement station or a first storage station). The process 300 continues with operation 306, wherein the AMHS vehicle is transported on transport rails to a second position (e.g., a second processing station, a second measurement station or a second storage station). The FOUP can be directly transferred to a piece of equipment to perform a next processing or measurement step if the equipment is not occupied, to a storage station of the corresponding process bay if the equipment is busy, or out of the fabrication facility. The process 300 further continues with operation 308, wherein a plurality of sensors and detectors are triggered by the host computer to conduct continuous and real-time monitoring of environment and security in the semiconductor fabrication facility (e.g., at different process bays, at certain station, etc.). Data from the plurality of sensors and detectors can be transmitted back to the host computer for processing through a nearby wireless router, according to certain embodiments. In some embodiments, the AMHS vehicles may stop during transporting on the transport rail to collect air samples for measurement depending on the type of measurement, response time of the detector and contaminant concentrations. In some embodiments, the AMHS vehicle can make a plurality of stops along the way for the purpose of sample collection and data measurement. Finally, the process 300 continues with operation 310, wherein the AMHS vehicle is transported and the FOUP is delivered to a second position. In some embodiments, the second position can be a second processing or measurement station, a second storage station for temporary storage of the wafers or out of the facility (e.g., packaging).

In an embodiment, a method for monitoring of environment and security in a fabrication facility, a method comprising: transporting an automated material handling system (AMHS) vehicle from a first position to a second position; and detecting at least one parameter using at least one sensor located on the AMHS vehicle to determine at least one environmental or security condition between the first and second positions.

Yet, in an embodiment, a system for monitoring of environment and security in a fabrication facility, a system comprising: a vehicle configured to automatically load, unload and transport at least one wafer, wherein the vehicle is configured to carry at least one sensor: wherein the at least one sensor is configured to determine at least one environmental or security condition while the vehicle is transported in a fabrication facility.

In another embodiment, a system for monitoring of environment and security in a fabrication facility, a system comprising: an automated vehicle; at least one contaminant sensor coupled to the automated vehicle; and at least one security sensor coupled to the automated vehicle.

Although the disclosure has been described in terms of exemplary embodiments, it is not limited thereto. Rather, the appended claims should be construed broadly, to include other variants and embodiments of the disclosure, which may be made by those of ordinary skill in the art without departing from the scope and range of equivalents of the disclosure.

What is claimed is:

1. A method for monitoring of environment and security in a fabrication facility, the method comprising:
    transporting an automated material handling system (AMHS) vehicle from a first position to a second position; and
    detecting at least one parameter using at least one sensor located on the AMHS vehicle to determine at least one environmental or security condition between the first and second positions, wherein the at least one environmental or security condition comprises contaminant levels/types of ionic species in air, wherein the ionic species in air comprise at least one of: $NH_4^+$, $Fe^{2+}$, $Fe^{3+}$, $Na^+$, $F^-$, $Cl^-$, $NO_3^-$, $PO_4^{3-}$, $SO_4^{2-}$, or $NO_2^-$.

2. The method of claim 1, further comprising:
    transporting the AMHS vehicle on an overhead transport rail.

3. The method of claim 1, wherein the AMHS vehicle is configured to load, unload and transport a plurality of wafers from the first position to the second position.

4. The method of claim 1, wherein the at least one sensor comprises at least one of: a humidity sensor, a temperature sensor, a magnetic field sensor, an ionic contaminant detector, an organic contaminant detector, a camera, or a radio frequency signal detector.

5. The method of claim 1, wherein the at least one environmental or security condition further comprises at least one of: temperature, humidity, magnetic field strength/direction, contaminant levels/types of organic species in air, unauthorized persons/activities, or unauthorized wireless communications.

6. The method of claim 5, wherein the organic species in air comprise at least one of: acetone/IPA, Propylene Glycol Methyl Ether (PGME), toluene, or propylene glycol monomethyl ether acetate (PGMEA).

7. The method of claim 5, wherein the unauthorized wireless communications comprises at least one of: communications using cellular signals, GPS signals, Wi-Fi signals, Bluetooth signals, or radio signals.

8. The method of claim 1, further comprising
    transmitting the at least one detected parameter to a host computer through a wireless communication network.

9. A system for monitoring of environment and security in a fabrication facility, the system comprising:
    a vehicle configured to load, unload and transport at least one wafer, wherein the vehicle is configured to carry at least one sensor, wherein the at least one sensor is configured to determine at least one environmental or security condition while the vehicle is transported in a fabrication facility, wherein the at least one environmental or security condition comprises contaminant levels/types of ionic species in air, wherein the ionic species in air comprise at least one of: $NH_4^+$, $Fe^{2+}$, $Fe^{3+}$, $Na^+$, $F^-$, $Cl^-$, $NO_3^-$, $PO_4^{3-}$, $SO_4^{2-}$, or $NO_2^-$.

10. The system of claim 9, wherein the vehicle is an automated material handling system (AMHS) transportation vehicle.

11. The system of claim 9, wherein the at least one sensor comprises at least one of: a humidity sensor, a temperature sensor, a magnetic field sensor, an ionic contaminant detector, an organic contaminant detector, a camera, or a radio frequency signal detector.

12. The system of claim 9, wherein the at least one environmental or security condition further comprises at least one of: temperature, humidity, magnetic field strength/direction, contaminant levels/types of organic species in air, unauthorized persons/activities, or unauthorized wireless communications.

13. The system of claim 12, wherein the organic species in air comprise at least one of: acetone/IPA, Propylene Glycol Methyl Ether (PGME), toluene, or propylene glycol monomethyl ether acetate (PGMEA).

14. The system of claim 12, wherein the unauthorized wireless communications comprise at least one of: communications using cellular signals, GPS signals, Wi-Fi signals, Bluetooth signals, or radio signals.

15. The system of claim 9, further comprises
    a control unit configured to control the vehicle and the at least one sensor;
    a data processing unit configured to receive data from the at least one sensor; and
    a host computer.

16. A system for monitoring of environment and security in a fabrication facility, the system comprising:
    an automated vehicle;
    at least one contaminant sensor coupled to the automated vehicle; and
    at least one security sensor coupled to the automated vehicle, wherein the at least one contaminant sensor is configured to detect ionic species in air within a fabrication facility wherein the ionic species in air comprises at least one of: $NH_4^+$, $Fe^{2+}$, $Fe^{3+}$, $Na^+$, $F^-$, $Cl^-$, $NO_3^-$, $PO_4^{3-}$, $SO_4^{2-}$, or $NO_2^-$.

17. The system of claim 16, wherein the at least one contaminant sensor is further configured to detect organic contaminants in air within a fabrication facility.

18. The system of claim 16, wherein the at least one security sensor is configured to detect at least one security parameters including unauthorized persons and wireless communications.

19. The system of claim 17, wherein the organic contaminants in air comprise at least one of: acetone/IPA, Propylene Glycol Methyl Ether (PGME), toluene, or propylene glycol monomethyl ether acetate (PGMEA).

20. The system of claim 18, wherein the wireless communications comprise at least one of: communications using cellular signals, GPS signals, Wi-Fi signals, Bluetooth signals, or radio signals.

* * * * *